US008062226B2

(12) United States Patent
Moore

(10) Patent No.: US 8,062,226 B2
(45) Date of Patent: Nov. 22, 2011

(54) TELESCOPE FOR AN IMAGING CATHETER

(75) Inventor: Thomas C. Moore, Livermore, CA (US)

(73) Assignee: Silicon Valley Medical Instruments, Inc., Fremont, CA (US)

(*) Notice: Subject to any disclaimer, the term of this patent is extended or adjusted under 35 U.S.C. 154(b) by 436 days.

(21) Appl. No.: 12/336,441

(22) Filed: Dec. 16, 2008

(65) Prior Publication Data

US 2009/0156941 A1 Jun. 18, 2009

Related U.S. Application Data

(60) Provisional application No. 61/008,120, filed on Dec. 17, 2007.

(51) Int. Cl.
*A61B 8/14* (2006.01)
*A61B 6/00* (2006.01)
(52) U.S. Cl. ................ 600/467; 600/466; 600/476
(58) Field of Classification Search .......... 600/407, 600/445, 463, 466, 467, 433, 424, 437, 439, 600/459, 462, 471, 585; 604/131, 264
See application file for complete search history.

(56) References Cited

U.S. PATENT DOCUMENTS

| 5,348,017 | A | * | 9/1994 | Thornton et al. | 600/467 |
| 6,004,271 | A | * | 12/1999 | Moore | 600/445 |
| 7,155,272 | B2 | | 12/2006 | Yamaguchi et al. | |
| 7,235,088 | B2 | | 6/2007 | Pintor et al. | |
| 7,269,453 | B2 | | 9/2007 | Mogul | |
| 7,485,127 | B2 | * | 2/2009 | Nistal | 606/180 |

OTHER PUBLICATIONS

International Search Report for International Application No. PCT/US2008/087203, conducted by the Korean Intellectual Property Office dated Apr. 27, 2009.

* cited by examiner

*Primary Examiner* — Michael Rozanski
(74) *Attorney, Agent, or Firm* — Richard O. Gray, Jr.; Graybeal Jackson LLP

(57) ABSTRACT

A catheter has a proximal end and a distal end and comprises an outer tube having a proximal end, an inner sheath slidingly received within the outer tube and extending distally from the outer tube, and a rotatable shaft extending from the proximal end of the outer tube to within the inner sheath. The rotatable shaft is axially fixed with respect to the outer tube and axially moveable within and with respect to the inner sheath. The rotatable shaft includes a proximal substantially rigid section and a distal flexible section. The catheter further includes a working element carried on the distal flexible section of the rotatable shaft.

11 Claims, 3 Drawing Sheets

PRIOR ART (Drive cable "S" curve)

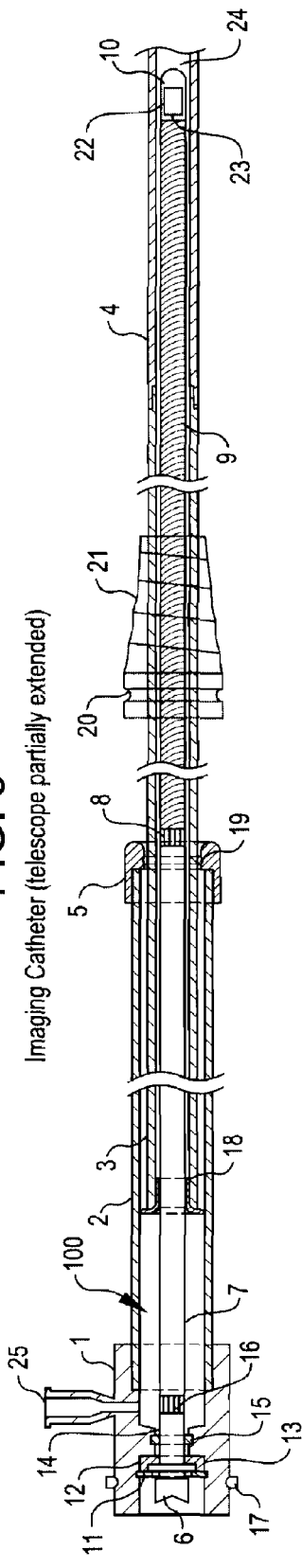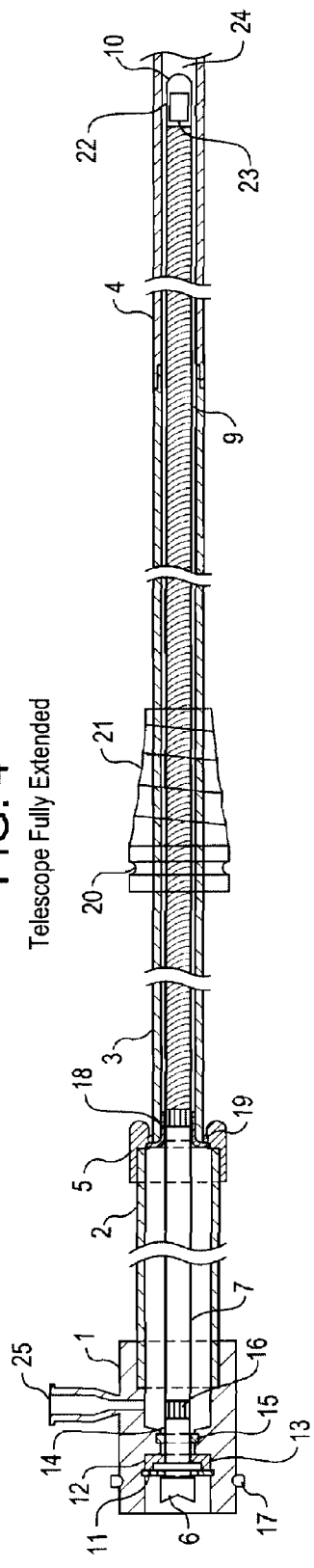

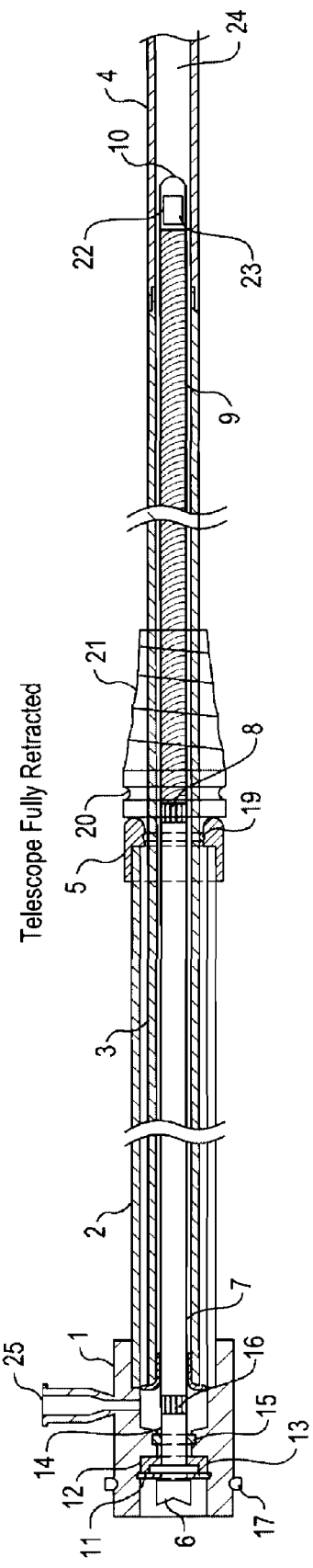
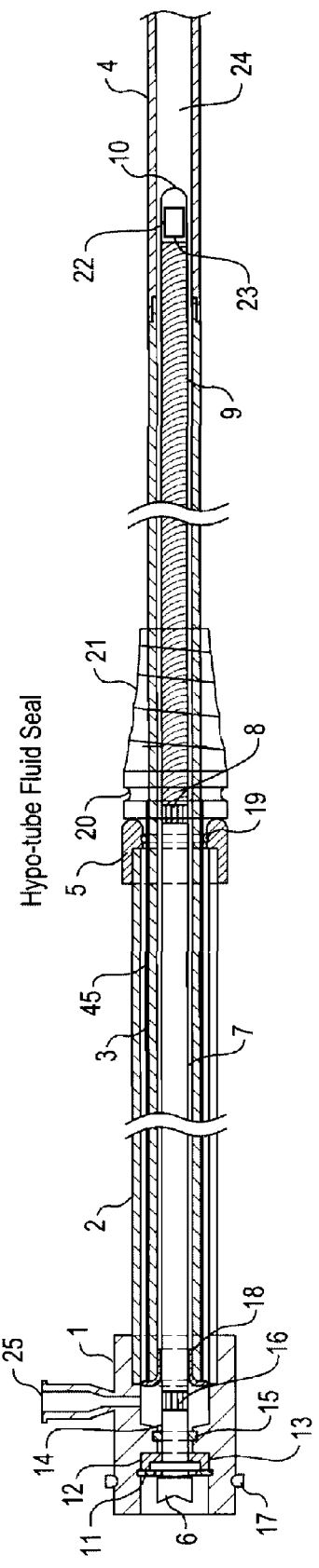

TELESCOPE FOR AN IMAGING CATHETER

PRIORITY CLAIM

The present application claims the benefit of copending U.S. Provisional Patent Application Ser. No. 61/008,120, filed Dec. 17, 2007, which application is incorporated herein by reference in its entirety.

BACKGROUND OF THE INVENTION

Intravascular ultrasound (IVUS) catheters provide a means of imaging internal structures in the body. Coronary IVUS catheters are used in the small coronary arteries of the heart to visualize coronary artery disease (CAD). There are other non-IVUS invasive imaging systems and catheters, such as optical coherence tomography OCT and Optical Frequency Domain Imaging (OFDI), that also provide a means of imaging internal structures within the human body. IVUS catheters (see FIG. 1) use transducers 46 to create pressure waves, other imaging systems use different imaging energy sources. Both OCT and OFDI use laser light as the imaging source.

There are two type of coronary IVUS catheters: mechanically scanned and electronically scanned. Mechanically scanned IVUS catheters mechanically spin the ultrasonic beam to sweep across a region of interest in the body. There are two generally accepted ways to do this. One is to mechanically rotate the transducer (FIG. 1) that generates the ultrasound beam. The other is to mechanically rotate a reflective surface or mirror that directs the beam from a stationary transducer into the desired swept pattern.

The preferred method is to rotate the transducer for the following reasons: Mirror based systems have additional imaging artifacts in their images as the beam is swept past mechanical supporting structures. Mirror based systems are generally larger then rotating transducer systems.

Electronically scanned catheters utilize a transducer array that electronically steers the ultrasound beam. In order to maximize the size of the transducer array, electronically scanning IVUS catheters locate the transducer array on the outside of the sheath. Mechanically scanning IVUS catheters locate the transducer on the inside of a sheath.

Mechanically scanning IVUS catheters FIG. 1 have two key advantages over electronically scanning IVUS catheters. Mechanically scanning IVUS catheter transducers 46 can operate at higher frequency then electronically scanning transducers. Therefore they have higher resolution. Mechanically scanning imaging catheters operate within an ultrasonically transparent sheath 28. The sheath prevents rotating components 33 and 34 from coming into contact with the patient's tissue and causing trauma. In addition, the sheath provides a lumen 49 that facilitates the movement of the imaging element along a portion of the distal length of the imaging catheter. Therefore, with a sheathed mechanical scanning IVUS catheter a volume of image data can be acquired over a region of interest without physically moving the catheter sheath 27 and 28 within the body.

Mechanically scanning IVUS imaging catheters contain drive cables 33 to "spin" the transducer 46 within the sheath 26 and 28. Drive cables are currently assembled by winding multiple strands of metal wire on a mandrel to create a long spring containing a repeating series of concentric rings, or windings, of the wire. Two, or more, springs are wound for each drive cable sized one to fit over the other. Adjacent springs are wound in the opposite direction of each other so that the grooves between the windings do not line up and lock together. During assembly, the inner spring is inserted into the outer spring still on its winding mandrel and then released so that it expands into the outer spring. In this way, the drive cable is extremely flexible in order to navigate small tortuous distal coronary anatomy while still providing some degree of torsional rigidity between the proximal driving end and the distal end containing the transducer.

Proximal housing 25 contains engagement pins 38 (×2) that mechanically mate to the imaging system catheter interface port. Within proximal housing 25 is a connector 30 which couples in mechanical energy to the drive cable 33 and electrical energy into the transmission line 47 within the drive cable. Connector 30 is fixedly connected to drive shaft 31, such that when rotated by the imaging system, drive shaft 31 is similarly rotated. Internal drive shaft 31 has a smooth bearing surface 37 which provides the running surface for rotational bearing 36 and snap ring 35. Snap ring 35 is fixedly held in place by the groove in proximal housing 25. A fluid seal 39 prevents fluids from the lumen 49, which runs the length of the catheter, from getting into the connector 30. The distal end of internal drive shaft 31 is connected via solder, brazing, welding or gluing bond joints 32 to the drive cable 33, such that when drive shaft 31 is rotated, drive cable 33 is similarly rotated.

Connector 30 within proximal housing 25 contains an electrical interface to couple in rotating electrical energy into the transmission line 47 that is disposed within drive cable 33 and runs its entire length. Transmission line 47 couples transmit energy from the system via connector 30, through the drive cable 33, and to the transducer 46 located within the distal housing 34. The electrical excitation energy causes transducer 46 to generate a pressure wave into the lumen 49 which is filled with saline via flushing port 40. The ultrasonic energy is coupled via the saline into the ultrasonically transparent portion of the sheath 28 and into the body. Objects in the body having acoustic impedance variations reflect back a portion of the ultrasonic pressure wave which is received by the transducer 46 after passing through sheath 28 and the saline filled lumen 49. Transducer 46 converts the received pressure signals into electrical signals which are coupled via transmission line 47 back to connector 30 and into the imaging systems' receiver. The system converts a series of scan lines acquired in the polar (R, θ) coordinate system, (similar to a beam from a lighthouse) into a slice or frame of image data by converting the polar scan lines into the Cartesian (X,Y) coordinate system for display on a X-Y scanning monitor, thus completing one rotation of the connector 30, drive shaft 31, drive cable 33, and distal housing 34.

In order to move, or translate, the rotating transducer 46 along the distal portion of the length of the lumen 49, a telescopic section is added at the proximal end of the catheter. The telescopic section contains inner proximal tubular element 26, outer distal tubular element 50, and anchor housing 29. The distal end of inner proximal tubular element 26 contains an end stop 51 to prevent the inner proximal tubular element 26 from disengaging from the outer distal tubular member 50 when the telescope is fully extended. Fluid seal 41, inside anchor housing 29 prevents fluids from lumen 49 from leaking out via the space between inner proximal tubular element 26 and outer distal tubular element 50. Groove 52 in anchor housing 29 provides a connection point for motorized (controlled) movement of the distal outer tubular element relative to the proximal housing 25.

Due to the flexible nature of the drive cable 33, the telescope 26, 29, and 50, and sheath 27 and 28 must provide a running surface to support drive cable 33 when it is rotating. It is also important to note that drive cable 33 is of a fixed length, so that when the outer distal tubular element 50 is translated relative to the inner proximal tubular member 26, the transducer 46 is translated relative to the distal sheath 28. In this way, the transducer 46 is moved along the length of the sheath 28 to acquire a volume of image data.

Current telescopic devices on IVUS catheters have several shortcomings. The current telescopes design is based on a proximal inner tubular member 26 that has an inside diameter sized to accommodate the drive cable 33 and provide sufficient clearance for flushing fluid. Flushing fluid is injected into flushing port 40 to fill lumen 49, in order to couple ultrasound energy from transducer 46, through the fluid to sheath 28 and thereby into the patient's body. The wall thickness and therefore the outer diameter of proximal inner tubular element 26 is sized in order to provide adequate structural integrity to support the forces occurring during the movement of the telescopic section in order to reduce the likelihood of any kinking or collapsing of the inner lumen onto the spinning drive cable 33. If the inner lumen of inner proximal tubular element compresses and catches drive cable 33 while it is spinning, the electrical connections of transmission line 47 will be severed and the imaging catheter will no longer function. A competing requirement to keep the wall thickness as thin as possible exists in order to reduce the gap between the outside diameter of drive cable 33 and the inside diameter of outer distal tubular member 50, which will be further elaborated in the description of the current design shortcoming below.

The outer distal telescopic tubular member 50 is attached at its proximal end to anchor housing 29 which contains fluid seal 41. Fluid seal 41, applies pressure to inner proximal tubular member 26. For this reason, inner proximal tubular member 26 must have a smooth outer surface along its entire length in order to form a fluid seal. The distal end of the outer distal tubular member is bonded via glue 43, to strain relief 44 and proximal shaft 27, which is part of the catheter sheath 28. The inside diameter of the outer distal tubular member 50, is sized to accommodate the outside diameter of end stop 51 which must be larger than the outside diameter of the inner proximal tubular member 27. Therefore, the inside diameter of the outer distal tubular member 50 is larger then the outside diameter of the inner proximal tubular member 26. This creates a significant gap between the outside diameter of drive cable 33 compared to the inside diameter of the outer proximal tubular member 50.

This gap is a major deficiency of the current design. When the telescope is fully extended, the transducer is in its most proximal location within sheath 28. Since the lumen 49 is filled with saline, the distal housing 34 and drive cable 33, must displace this fluid as the telescope is retracted and the transducer 46 is advanced into the sheath 28. This creates a backward force on drive cable 33. Due to the gap between drive cable 33 and the outer proximal tubular member 50 and the flexible nature of drive cable 33, drive cable 33 is compressed into an "S" curve as shown in FIG. 2. This "S" curve pulls the location of transducer 46 inward, thereby scanning the incorrect region of the anatomy and often leads to the drive cable 33 folding back over onto itself. When the drive cable 33 folds back over onto itself, the electrical connections of transmission line 47 are severed and the imaging catheter is rendered inoperative. Approximately 1% of all IVUS catheters used are returned as defected units as a result of this failure mechanism.

Another short coming of existing telescope designs is that the telescope is not straight, which makes it difficult to extend and retract the telescope. This occurs because the telescope is made of polymers for cost reasons, and the inner proximal tubular member's 26 wall thickness is kept thin to keep the outside diameter of the outer telescope member as small as possible. The resultant thin wall polymer is then coiled into its packaging and during sterilization and normal shelf aging, the polymer takes a set in the coiled (non-straight) position.

Another short coming of existing telescopes is the fluid seal 41 and inner proximal tubular member 26 outer running surface. The fluid seal must prevent saline from escaping during catheter flushing operations. This fluid seal is subject to pressures up 150 PSI. Current telescopic sections are made from polymers that do not have a smooth running surface for the fluid seal to slide against during telescopic action. As a result, the pressure on the fluid seal is increased to insure the seal holds against the flushing pressure. This in turn increases the friction that must be overcome when the telescope is extended or retracted. As a result, the existing telescope design is difficult to extend and retract. Another failure mechanism occurs when the user forces the outer distal tubular member 50 downward onto the inner proximal tubular member 26 which is not straight and the inner tubular member is kinked. This results in either a failed electrical connection or a mechanical defect in the drive cable which manifests itself in a non-uniformed rotation of the transducer and the associated image artifact.

Another short coming of existing telescope design is the cost. The current design contains three separate tubular members which need to be individually bonded to form the telescope and this adds unnecessary cost to the assembly. The three components are the inner proximal tubular member 26, the outer distal tubular member 50 and the proximal shaft 27 of the catheter which is bonded to the distal end of the outer proximal tubular telescopic member.

A short coming of the existing drive cable 33 design is that it is flexible its entire length. This results in several shortcomings. The drive cable 33 can fail by folding back on itself as described above. The drive cable can fold back in the above S shape, while not failing, it pulls back the transducer 46 proximally so that it is pointing at a more proximal region of the artery then it should. This results in errors in length measurements on the system which is not aware of the fold hack condition. The flexible drive cable lacks torsional stiffness which can results in erratic rotational velocity of the imaging element. Erratic rotational velocity of the imaging element produces distortions in the image.

SUMMARY

According to one embodiment, a catheter has a proximal end and a distal end and comprises an outer tube having a proximal end, an inner sheath slidingly received within the outer tube and extending distally from the outer tube, and a rotatable shaft extending from the proximal end of the outer tube to within the inner sheath. The rotatable shaft is axially fixed with respect to the outer tube and is axially moveable within and with respect to the inner sheath. The rotatable shaft includes a proximal substantially rigid section and a distal flexible section. The catheter further includes a working element carried on the distal flexible section of the rotatable shaft.

The proximal rigid section of the rotatable shaft is comprised of a biocompatible material such as, for example, stainless steel.

The outer tube may have a distal end sealingly engaged with the inner sheath. The rigid section of the rotatable shaft and the flexible section of the rotatable shaft may be joined at a joint substantially adjacent the distal end of the outer tube.

In another embodiment, the inner sheath has a proximal portion and the catheter further includes a substantially rigid cover extending over the proximal portion of the inner sheath.

The substantially rigid cover is preferably formed of a biocompatible material such as, for example, stainless steel.

According to a further aspect of the invention, the catheter may further include a seal that provides a fluid seal between the inner sheath and the outer tube. The outer tube has a distal end and the seal may be at the distal end of the outer tube.

The working element may be an optical element or a transducer.

BRIEF DESCRIPTION OF THE DRAWINGS

The features of the present invention which are believed to be novel are set forth with particularity herein. The invention, together with further features and advantages thereof, may best be understood by making reference to the following description taken in conjunction with the accompanying drawings, in the several figures of which like reference numerals identify identical elements, and wherein:

FIG. 3 is a sectional view of an intravascular catheter embodying the present invention shown in a partially extended configuration;

FIG. 4 is a sectional view of the intravascular catheter of FIG. 3 shown in a fully extended configuration;

FIG. 5 is a sectional view of the intravascular catheter of FIG. 3 shown in a fully retracted configuration; and FIG. 6 is a sectional view of another intravascular catheter embodying the present invention that includes a hypo-tube fluid seal.

DETAILED DESCRIPTION OF THE INVENTION

Figure 1:
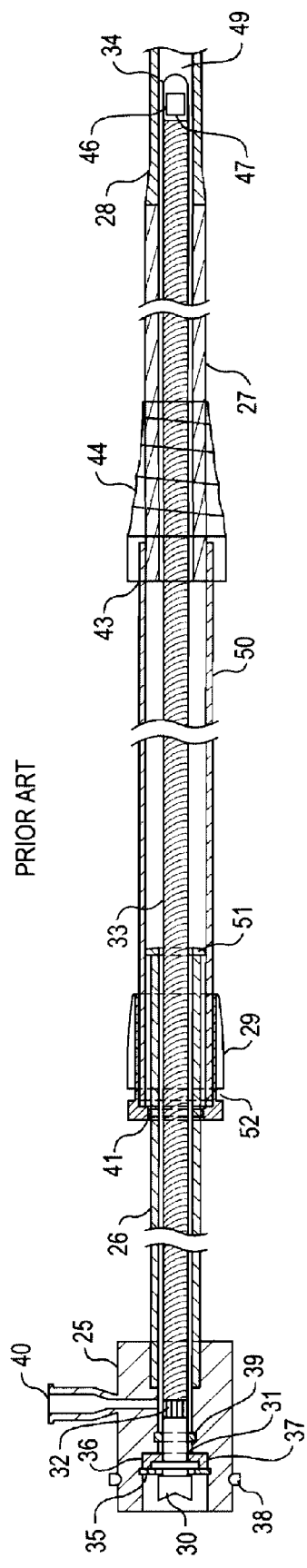
FIG. 1 is a sectional side view of a prior art intravascular catheter of the type which may be improved upon by the present invention.
Figure 2:
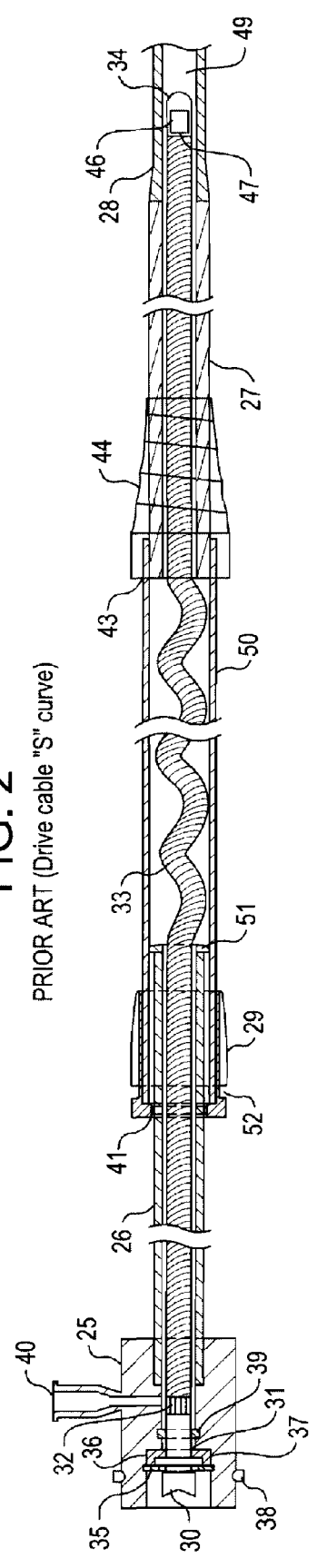
FIG. 2 is another sectional side view of the prior art intravascular catheter of FIG. 1.

As will be seen from the foregoing, the embodiments of the present invention shown in FIGS. 3-6 include improvements to both the drive cable 7, 8 and 9 and the telescope. These improvements make it possible, without limitation, to eliminate failure mechanisms associated with collapsing of the telescope lumen onto the drive cable, to eliminate drive cable failures resulting from drive cable fold back in the telescoping section, to reduce friction within the telescope to improve its operation and to eliminate unnecessary components in the telescope section.

The drive cable 100, according to these embodiments of the present invention, contains both a proximal rigid section 7 and a distal flexible section 9. The rigid section is constructed of a stainless steel or other suitable material hypo tube that is welded or in some other way bonded to the flexible drive cable 9 that is similar to those used in current mechanically scanning imaging catheter designs. The rigid section 7 is welded or in some other fashion bonded 16 to the drive shaft 14 which is fixedly connected to connector 6. The length of the rigid section 7 of the drive cable 100 is such that the bond joint 8 to the flexible section of the drive cable 9 is distal to, at or near the distal end of the outer proximal telescoping tubular member 2. This bond location is intended to insure that a substantial portion of the flexible section 9 of the drive cable 7, 8 and 9, does not enter into the telescoping section of the catheter.

In operation according to various aspects of the present invention, the proximal housing 1 contains engagement pins 17 that mechanically mate to the imaging system catheter interface port. Within proximal housing 1 is a connector 6 which couples in mechanical energy to the drive cable 100 and electrical energy into the transmission line 23 within the drive cable. Connector 6 is fixedly connected to drive shaft 14, such that when rotated by the imaging system, drive shaft 14 is similarly rotated. Internal drive shaft 14 has a smooth bearing surface 13 which provides the running surface for rotational bearing 12 and snap ring 11. Snap ring 11 is fixedly held in place by the groove in proximal housing 1. A fluid seal 15 prevents fluids from the lumen 24, which runs the length of the catheter, from getting into the connector 6. The distal end of drive shaft 14 is connected via solder, brazing, welding or gluing bond joints 16 to the drive shaft 100, such that when drive shaft 14 is rotated, drive cable 100 is similarly rotated. The drive cable 100 carries at its distal end a working element. Here the working element is an ultrasonic transducer 22. As may be appreciated, the working element could alternatively be an optical mirror or an optical lens, depending on the intended use of the catheter. If the working element is an optical element such as a mirror or lens, the transmission line 23 would then be replaced by an optical fiber, for example.

Connector 6 within proximal housing 1 contains an electrical interface to couple in rotating electrical energy into the transmission line 23 that is disposed within drive cable 100 and runs its entire length. Transmission line 23 couples transmit energy from the system via connector 6, through the drive cable 100, and to the transducer 22 located within the distal housing 10. The electrical excitation energy causes transducer 22 to generate a pressure wave into the lumen 24 which is filled with saline via flushing port 25. The ultrasonic energy is coupled via the saline into the ultrasonically transparent portion of the sheath 4 and into the body. Objects in the body having acoustic impedance variations reflect back a portion of the ultrasonic pressure wave which is received by the transducer 22 after passing through sheath 4 and the saline filled lumen 24. Transducer 22 converts the received pressure signals into electrical signals which are coupled via transmission line 23 back to connector 6 and into the imaging systems' receiver. The system converts a series of scan lines acquired in the polar (R, θ) coordinate system, (similar to a beam from a lighthouse) into a slice or frame of image data by converting the polar scan lines into the Cartesian (X,Y) coordinate system for display on a X-Y scanning monitor, thus completing one rotation of the connector 6, drive shaft 14, drive cable 7, 8 and 9, and distal housing 10.

In order to move, or translate, the rotating transducer 22 along the distal portion of the length of the lumen 24, a telescopic section is added at the proximal end of the catheter. The telescopic section contains outer proximal tubular member 2, end cap 5, and the proximal sheath 3 which slides into the outer proximal tubular member 2. The proximal end of proximal sheath 3 contains an end stop 18 to prevent the proximal sheath 3 from disengaging the outer proximal shaft 2 when the telescope is fully extended. Fluid seal 19, is located inside end cap 5 and prevents fluids from lumen 24 from leaking out via the space between outer proximal tubular element 2 and the proximal sheath 3. Strain relief 21 contains groove 20 which provides the connection point for motorized (controlled) movement of the telescoping section. As is well known, the sheath 4, including proximal sheath 3 is formed of a biocompatible flexible material.

Due to the rigid nature of the rigid section 7 of the drive cable 100, a running surface is not required along the entire length of this section of the drive cable as is required in the prior art. Therefore the end stop 18, bearing 12 and lock washer 11 provide the required running surfaces along this segment of the drive cable. As can be seen in FIG. 4, when the telescope is fully extended the two running surfaces for the rigid segment 7 of the drive cable 100 are at either ends of rigid segment 7. When the telescope is fully retracted, the two running surfaces are at the proximal end of the rigid section 7 of drive cable 100. It is important to note that drive cable 100 is of a fixed length, so that when the proximal sheath 3 is translated relative to the outer proximal tubular member 2, the transducer 22 is translated relative to the distal sheath 4. In this way, the transducer 2 is moved along a portion of the length of the sheath 4 to acquire a volume of image data.

By virtue of the present invention, as described in the context of the illustrated embodiments, the outer proximal tubular member 2 wall thickness is no longer constrained by the need to slide into another segment of the telescope. Therefore the wall thickness can be increased to insure that the inner lumen can not collapse onto the spinning drive cable 100 and cause either image distortions or catheter failure. In addition, the thick wall of the outer proximal tubular member 2 will insure that the telescoping section remains straight at all times. This will improve the sliding action of the telescope. Converting the proximal most section of the telescope from an inner member to an outer member eliminates the need for an outer distal tubular member thereby reducing the part count and number of bond joint required to assembly the telescope section.

The rigid section 7 of drive cable 100, prevents the occurrence of the "S" curve in the drive cable when the drive cable is advance. This prevents the possibility of drive cable fold back and subsequent failure of the electrical connection. This improvement is expected to reduce field failure rates of mechanically scanning invasive imaging catheters significantly.

Optionally, a stainless steel hypo tube 45 or other suitable rigid material can be placed over the proximal sheath 3. This provides a smooth running surface for fluid seal 19.

While particular embodiments of the present invention have been shown and described, modifications may be made, and it is therefore intended to cover in the appended claims, all such changes and modifications which fall within the true spirit and scope of the invention as defined by those claims.

What is claimed:

1. A catheter having a proximal end and a distal end comprising:
   an outer tube having a proximal end and a distal end;
   an inner sheath slidingly received within the outer tube and extending distally from the outer tube distal end;
   a rotatable shaft extending from the proximal end of the outer tube to within the inner sheath, the rotatable shaft being longitudinally fixed with respect to the outer tube and the outer tube and the rotatable shaft being longitudinally moveable with respect to the inner sheath, the rotatable shaft including a proximal substantially rigid section and a distal flexible section; and
   a working element carried on the distal flexible section of the rotatable shaft.

2. The catheter of claim 1, wherein the proximal rigid section of the rotatable shaft is comprised of a biocompatible material.

3. The catheter of claim 1, wherein the proximal rigid section of the rotatable shaft is comprised of stainless steel.

4. The catheter of claim 1, wherein the distal end of the outer tube is sealingly engaged with the inner sheath, and wherein the rigid section of the rotatable shaft and the flexible section of the rotatable shaft are joined at a joint substantially adjacent the distal end of the outer tube.

5. The catheter of claim 1, wherein the inner sheath has a proximal portion and wherein the catheter further includes a substantially rigid cover extending over the proximal portion of the inner sheath.

6. The catheter of claim 5, wherein the substantially rigid cover is formed of a biocompatible material.

7. The catheter of claim 5, wherein the substantially rigid cover is formed of stainless steel.

8. The catheter of claim 1, further including a seal that provides a fluid seal between the inner sheath and the outer tube.

9. The catheter of claim 8, wherein the seal is at the distal end of the outer tube.

10. The catheter of claim 1, wherein the working element comprises a transducer.

11. The catheter of claim 1, wherein the working element comprises an optical element.

* * * * *